United States Patent [19]
Mendizabal

[11] Patent Number: 5,747,068
[45] Date of Patent: May 5, 1998

[54] FLOUXETINE PHARMACEUTICAL FORMULATIONS

[75] Inventor: Flavia Arce Mendizabal, Madrid, Spain

[73] Assignee: Lilly S. A., Madrid, Spain

[21] Appl. No.: 503,570

[22] Filed: Jul. 18, 1995

[30] Foreign Application Priority Data

Jul. 20, 1994 [ES] Spain ............... 9401593

[51] Int. Cl.$^6$ .......... A61K 9/20; A61K 9/46; C07C 91/22; C07C 93/06
[52] U.S. Cl. .......... 424/465; 514/777; 514/778; 424/466; 424/44
[58] Field of Search .......... 424/44, 465

[56] References Cited

U.S. PATENT DOCUMENTS

| | | | |
|---|---|---|---|
| 3,034,911 | 5/1962 | McKee et al. | 106/210 |
| 3,091,574 | 5/1963 | Coletta et al. | 167/82 |
| 3,424,842 | 1/1969 | Nurnberg | 424/94 |
| 3,622,677 | 11/1971 | Short et al. | 424/361 |
| 3,679,794 | 7/1972 | Bentholm et al. | 424/148 |
| 3,725,556 | 4/1973 | Hanssen et al. | 424/357 |
| 3,852,421 | 12/1974 | Koyanagi et al. | 424/94 |
| 4,061,747 | 12/1977 | Eriksoo et al. | 424/244 |
| 4,194,009 | 3/1980 | Molloy et al. | |
| 4,314,081 | 2/1982 | Molloy et al. | |
| 4,666,703 | 5/1987 | Kupf | 424/470 |
| 4,886,669 | 12/1989 | Ventouras | 424/469 |
| 5,420,156 | 5/1995 | Harfenist et al. | 514/434 |
| 5,464,632 | 11/1995 | Cousin et al. | 424/465 |

FOREIGN PATENT DOCUMENTS 0 365 480   10/1989   European Pat. Off. .

OTHER PUBLICATIONS

British Pharmacopoeia, 1993, vol. II.

*Primary Examiner*—Shep K. Rose
*Attorney, Agent, or Firm*—Robert D. Titus; David E. Boone

[57] ABSTRACT

Pharmaceutical formulations of fluoxetine or an acid addition salt thereof, suitable for manufacturing dispersible tablets by direct compression and comprising, in addition to the active ingredient, the appropriate excipients and coadjuvants, selected from among disintegrants, diluents, lubricants, anti-adherents, sweeteners, flavorings and, optionally, colorants.

Said formulations are suitable for manufacturing dispersible tablets which disintegrate in less than three minutes in water at 19° C.–21° C., and are appropriate for treatment of depression.

20 Claims, No Drawings

FLOUXETINE PHARMACEUTICAL FORMULATIONS

FIELD OF THE INVENTION

This invention refers to pharmaceutical formulations containing fluoxetine or an acid addition salt thereof, and which are suitable for the manufacture of solid, orally-administered pharmaceutical forms. In particular, the invention refers to pharmaceutical formulations and dispersible tablets containing fluoxetine or an acid addition salt thereof, particularly the hydrochloride, and their process of manufacture.

BACKGROUND OF THE INVENTION

Fluoxetine or N-methyl-3-(p-trifluormethylphenoxy)3-phenylpropylamine is an anti-depressant substance described, for example, in German patent no. DE 2,500,110 and U.S. Pat. No. 4,314,081 (Eli Lilly & Co.). The antidepressant action of fluoxetine appears to be based on its capacity to selectively inhibit the uptake of serotonin by the neurons of the central nervous system. Fluoxetine is especially indicated for the treatment of depression and its associated anxiety, and for the treatment of bulimia nervosa and obsessive-compulsive disorders. The currently available pharmaceutical forms for administration of fluoxetine, namely in the form of hydrochloride consist of capsules and, more recently, a solution.

The use of capsules presents a series of limitations and drawbacks, affecting the following:

Patient use, which may be limited by the fact that some patients may have difficulty in swallowing the capsule, particularly children and the elderly, who may in fact even be unable to swallow them.

Dosage, since only single dosage is possible. On the other hand, the administration of fluoxetine hydrochloride in solution form raises a series of drawbacks which may be summarised as follows:

Dosage of the active ingredient requiring the use of measuring devices which are not normally precise;

The limited scope for use in diabetic patients, who must take the appropriate precautions given the saccharose content of the syrup (approximately 60% weight/volume);

The risk of accidental overdose due to uncontrolled consumption, particularly in children; and The limited ease of handling and transport due to the volume involved, which is associated with a certain risk that therapy will not be completed, with the consequent loss of efficacy of treatment.

On the other hand, the treatment of depression requires on-going and extended consumption (between 2 and 6 months on average) of effective doses of anti-depressants such as fluoxetine. Fluoxetine hydrochloride has a strong bitter and unpleasant flavor, so that its administration in solution raises problems of patient acceptance when they are required to ingest it over long periods of time. As already pointed out, these problems may result in a failure to complete the therapy, which greatly reduces the efficacy of treatment. Therefore, in general, the existing forms of administration of fluoxetine hydrochloride do not completely satisfy some requisites which are considered desirable for treatment of depression and other related conditions, such as their usability with any patients, and organoleptic features which are not unpleasant to the patient.

There is therefore a need for new pharmaceutical forms of administration of fluoxetine which overcome these problems, facilitating their administration by the patient, which can be used with diabetic patients without additional difficulties, and which enhance the efficacy of treatment. This invention provides a solution to the problems referred to by providing new pharmaceutical formulations containing fluoxetine or an acid addition salt thereof, particularly the hydrochloride, with acceptable organoleptic characteristics and which are suitable for the manufacture of dispersible tablets.

Dispersible tablets are solid, orally-administered pharmaceutical forms which must dissolve in less than three minutes in water at 19° C.–21° C. and disperse evenly in water. The dispersion uniformity test involves placing two tablets in 100 ml of water and shaking them until they disperse completely. The dispersion produced by this means must pass through a screen with a nominal mesh of 710 microns (*Pharmacopea Britanica*, Vol. II, 1988).

Dispersible tablets are familiar which contain antibiotics (amoxycillin) and anti-inflammatories (piroxicam), but not containing an anti-depressant.

The subject of this invention is therefore pharmaceutical formulations containing fluoxetine or an acid addition salt thereof and which are suitable for the manufacture of dispersible tablets. An additional purpose of this invention concerns dispersible tablets containing fluoxetine hydrochloride and their process of manufacture.

DETAILED DESCRIPTION OF THE INVENTION

The preparation of suitable formulations for the manufacture of dispersible tablets requires study both of the physical-chemical incompatibilities of the active ingredient and a search for suitable excipients enabling the requirements of the various Pharinacopeas to be fulfilled. Account must likewise be taken of the process for the manufacture of the dispersible tablets to be used, since the excipients and coadjuvants of the formulation will depend in large part upon the process selected for the production of the dispersible tablets. For reasons to be set out below, the direct compression tablet manufacturing procedure is the one which has been chosen.

The parameters defining dispersible tablets are as follows:

i) Their high speed of disintegration in water, and ii) The uniformity of dispersion of the particles into which they disintegrate.

Disintegration rate and dispersion uniformity also depend both on the coadjuvants and the active ingredient. Thus disintegration as a measure of the release of active ingredient of compressed pharmaceutical preparations is the critical parameter in the development of dispersible forms, so that the selection of the coadjuvants in the preparation of dispersible tablets is the most important phase of the Galenic research. The properties and quality of the finished tablet depend largely on the coadjuvants it incorporates, making the selection of such coadjuvants of the greatest importance, as is the manufacturing process to be used, since the choice of coadjuvants depends on the technique employed.

The new pharmaceutical formulations of fluoxetine or an acid addition salt thereof, suitable for the manufacture of dispersible tablets as provided by this invention take the foregoing considerations into account and contain, in addition to the active ingredient, suitable quantities of disintegrants, diluents, lubricants, antiadherents, sweeteners, flavorings and, optionally, colorants.

The active ingredient of the formulations in this invention is fluoxetine. In the sense used in this description, the term "fluoxetine" includes free fluoxetine and the pharmaceutically acceptable acid addition salts thereof which meet the requirements of disintegration, including particularly and preferably the hydrochloride. Said active ingredient may be present in the formulation in a quantity of between 4% and 7.5% by weight in relation to the total weight of the formulation. The fluoxetine can be prepared as described for example in Spanish Patent No. ES 433,720 (Eli Lilly & Co.).

Because the dispersible tablet's critical parameter is its rate of disintegration in water, the selection of the appropriate disintegrant is one of the most important phases. In the sense used in this description, the term "disintegrant" refers to an agent which creates an increase in the surface so that the active ingredient of the tablet is released very quickly. Sodium starch glycolate, polymeric derivatives of acrylic acid and, preferably, crospovidone are suitable disintegrants for the formulations in this invention.

Sodium starch glycolate may be used in concentrations exceeding 5% by weight in relation to the total weight of the formulation, preferably at concentrations of between 9.5% and 17%, since below 5%, the volume increase caused by the swelling of the sodium starch glycolate is relatively large and causes rapid but insufficient disintegration.

Polymeric derivatives of acrylic acid can be used in proportions of between 10% and 21% of total formulation weight.

The preferred disintegrant is, as already indicated, a crospovidone (insoluble polyvinylpyrrolidone [PVP] obtained by polymerization of vinylpyrrolidone). This inflatable polymer can be included in the formulation in a proportion of between 9% and 13% by weight referred to total formulation weight. It is believed that the high disintegrating action of the reticulated and insoluble PVP is due to its hydration capacity (water adsorption) which means that a very rapid tablet disintegration rate is attained with the resulting enhancement of the dissolution of the fluoxetine in water.

On the other hand, the selection of the direct compression technique to manufacture dispersible tablets involves a further advantage in the choice of excipients. The possibility of using the disintegrant in extragranular form enhances its swelling effect since the disintegrating effect is not altered either by humectation or by drying.

In the sense used in this description, the term "diluents" includes excipients which facilitate the compression of powdery materials and give the tablets strength. Microcrystalline cellulose, lactose, hydroxypropyl cellulose (HPC), pregelatinized starch, dry flowing starch and mixtures thereof are suitable diluents.

The following are examples of suitable diluents for the formulations in this invention:

1) Mixtures of lactose and hydroxypropyl cellulose. Lactose is a disaccharide suitable for direct compression, since it produces tablets of great hardness; the HPC not only facilitates compression but also accelerates the disintegration of the tablet and acts as an exfoliant. Of existing HPCs, L-HPC (Low-Substituted Hydroxypropyl Cellulose) is preferred, particularly L-HPC 21, which is differentiated from classical HPCs by its low substitution rate and weak solubility in water. In these mixtures of lactose and HPC, the lactose can be used at a rate of approximately 40% by weight in relation to the total weight of the formulation, while the HPC is used at between 5% and 20% by weight in relation to total weight of the formulation.

2) Combinations of pregelatinized starch and L-HPC. Pregelatinized starch is a rapidly disintegrating modified starch with diluent and agglutinant capacity in direct compression. Pregelatinized starch can be added at between 60% and 70% by weight in relation to total weight of the formulation. The quantity of L-HPC may be approximately 5% by weight in relation to total weight of the formulation. Because of the flow characteristics of pregelatinized starch, lubricants need not be added to formulations containing it.

3) Microcrystalline cellulose and its mixtures with dry flowing starch. It has been confirmed that the preferred diluents for the formulations in this invention contain microcrystalline cellulose, whose characteristics of fluidity and compressibility are highly appropriate to the powder mix. Microcrystalline cellulose enables tablets to be manufactured with a high degree of purity using the direct compression technique. It also acts as a binder, to give strong tablets of suitable hardness, while its swelling capacity provides short disintegration times. Of the different types of microcrystalline cellulose available on the market, which include Avicel PH101 (mean particle size 50 microns) and Avicel PH102 (mean particle size 90 microns), preference is for the one identified as Avicel PH102 since, while both have similar characteristics in terms of their capacity to facilitate direct compression, Avicel PH102 facilitates direct compression of fine powder mixtures (as in the formulations of this invention) thanks to the fluidity it confers on the mixture due to its larger particle size.

The preferred diluent combination comprises microcrystalline cellulose (Avicel PH102) and dry flowing starch: the dry flowing starch may be present at between 15% and 27% by weight in relation to total formulation weight, and the microcrystalline cellulose between 46% and 58% by weight in relation to the total weight of the formulation. At very high cellulose percentages, of about 55%–58%, tablets were obtained with a weight of between 315 and 340 mg while, at somewhat lower percentages, of the order of 51%–54%, the tablets obtained had a final weight of between 300 and 350 mg. Finally, if the percentage of Avicel PH102 microcrystalline cellulose is between 46% and 48%, the final weight of the tablets is of some 310–340 mg.

The term "lubricant" as used in this description includes excipients which reduce inter-particle friction inside the tablet, reducing the reaction forces appearing on the walls of the matrix. Talcum may be used as lubricant suitable for the formulations in this invention or, for preference, stearyl sodium fumarate, a hydrophylic lubricant. This coadjuvant can be added to the formulations in this invention at a rate of between 1% and 2.5% by weight in relation to the total weight of the formulation.

The inclusion of this excipient enhances the slipping of the formulation to be compressed. It also ensures even filling of the space in the matrix so that there is very little tablet weight variation.

Standard stearic acid salts are not suitable since, for example, magnesium stearate does not adsorb water, giving a solution of most unpleasant appearance, with the formation of a "halo" on the surface, unlike stearyl sodium fumarate.

As has already been stated, formulations containing pregelatinized starch as diluent do not require the addition of lubricant.

The term "antiadherent" as used in this description includes excipients which prevent particle adhesion, so avoiding or reducing compacting and limiting friction between them. Colloidal silicone dioxide can be used as a suitable antiadherent for the formulations in this invention: because of its large specific surface, this raw material is a very good regulator of powder flow and also acts as adsorbent, capturing the humidity which would be taken up by the fluoxetine, so slowing the degradation of the active ingredient by hydrolysis.

This coadjuvant can be incorporated at a percentage of between 1% and 2% by weight in relation to total formulation weight.

The formulations in this invention may also contain sweeteners and flavorings since one of the major problems to be overcome was to provide these formulations with organoleptic characteristics (aroma and flavor) which would make them acceptable to patients. The active ingredient, fluoxetine, namely in the form of hydrochloride salt, has a very unpleasant sharply bitter flavor which must be masked for dissolved oral administration. To overcome this problem, the formulations in this invention include sweeteners and flavorings.

Sodium saccharin may be used as artificial sweetener at between 0.4% and 5% by weight in relation to total weight of the formulation, or aspartame of approximately 1.6% by weight in relation to total weight of the formulation.

The flavorings and/or aromas (powdered) which may be incorporated into these formulations in quantities of between 1.4% and 12.5% by weight in relation to total weight of the formulation are: mint aroma (54,234 TP0551 Firmenich), two different peppermint aromas (957,685 P0551 and 57,720 TP0551 Firmenich), orange flavoring (55,604 Firmenich), peach aroma (52,490 AP0551 Firmenich), apricot aroma (52,247 AP0551 Firmenich), raspberry aroma (52,381 AP0551 Firmenich), lemon aroma (502,336 TP0551 Firmenich), coconut aroma (54,385 AP0551 Firmenich), pineapple aroma (502,434 AP0551 Firmenich), strawberry, aniseed aromas and their mixtures.

Excipients may also be used which help to mask the bitterness produced by fluoxetine hydrochloride by means of their capacity to provide freshness to the formulation. In this sense, a combination of sodium saccharine may be used, included at between 0.5% and 4.5% by weight in relation to total weight of the formulation, and mannitol between 2.5% and 5% by weight in relation to total weight of the formulation.

These formulations may also incorporate sorbitol and ammonium glyciricinate as sweeteners, the former, the preferred natural sweetener, at between 1.5% and 4% by weight in relation to total weight of the formulation, and the latter between 0.5% and 1% by weight in relation to total weight of the formulation.

The preferred aromas for addition to the formulations prepared with mannitol and sorbitol are strawberry, at between 10% and 12% by weight in relation to total weight of the formulation; aniseed, at between 0.6% and 0.7% by weight in relation to total weight of the formulation; peppermint at approximately 0.3% by weight in relation to total weight of the formulation, and combinations of the last two, which give good fragrance to the final formulation and mask the bitterness of the active ingredient.

Additionally, and optionally, the formulations in this invention may contain a colorant agent to provide uniform color. Titanium dioxide (E-171) may be used as colorant. However, it is not necessary to add it, particularly if dry flowing starch is used as diluent, since this compound helps to provide a homogenous solution of pleasant appearance.

The fluoxetine formulations made available by this invention can be prepared easily, placing the appropriate amounts of the different excipients and coadjuvants, once screened, in a suitable mixer. The active ingredient is then added and mixed until it is homogenous, giving a powder which flows well.

These new formulations can be used to manufacture dispersible tablets containing fluoxetine or an acid addition salt thereof as the active ingredient.

As already stated, the manufacturing process for the tablet plays a very important role in the design of the pharmaceutical formulation. The formation of the tablet body may be based on a granulate (an agglomerated material made of powder particles to which an agglutinant is added), or on a powder mixture not previously treated (direct compression). The coadjuvants are selected according to the chosen technique.

Because dispersible tablets are very sensitive to damp and their stability is compromised by granulation operations, direct compression is the preferred technique, as the one with the most advantages: on the one hand, manufacture is rapid, depending neither on a granulation nor on a drying process and, on the other hand, it avoids possible degradation (due to hydrolysis) of the active ingredient, during granulation. Risk of contamination is also reduced. However, perhaps the most significant advantage is that directly compressed tablets normally disintegrate more rapidly than those made by wet granulation which require the addition of agglutinant agents which slow the disintegration rate.

While direct compression may cause some drawbacks, such as problems of uniformity of mixture and dosage, fluidity and compressibility, surprisingly, with the formulations in this invention, none of these problems arose. In fact, the tablets varied very little in weight and content of active ingredient. Compressibility was acceptable and tablet hardness was within the required limits.

Dispersible tablets containing fluoxetine or an acid addition salt thereof, particularly the hydrochloride may be manufactured by standard processes, for example in a conventional rotary or eccentric compressing machine which compresses the prepared and screened pharmaceutical formulation fed to the machine. Dispersible tablets containing fluoxetine provided by this invention are solid, intended for oral use, of uniform appearance, and with sufficient mechanical strength to bear possible damage from storage and transport. The active ingredient is distributed evenly in the pharmaceutical form and the disintegration rate in water is high (within three minutes in water at 19° C.–21° C.). Likewise, the level of disintegration (or fineness of the particles in to which the product disintegrates) is suitable, and in line with the requirements of the various Pharmacopeas.

The use of dispersible tablets containing fluoxetine hydrochloride presents a series of benefits over known forms of administration of fluoxetine hydrochloride (capsules and solution) including the following:

They are suitable to treat patients with difficulties for ingesting solid forms.

They may be used by diabetic patients since they do not contain saccharose as sweetener.

Dosage is flexible and reasonably accurate following dissolution in the volume of water desired by the patient.

Their solutions are of suitable organoleptic characteristics, acceptable to patients.

Their shape, size and reduced volume allow them to be presented in blister form, which is a benefit to the patient, enhancing ease of handling and carrying, to ensure that the patient completes the therapy and so raising the efficacy of the treatment.

And the risk is diminished of accidental overdose, making them less hazardous, particularly to children.

The following Examples illustrate specific implementations of the invention and should not be construed as limiting it. Said Examples use Kirsch Pharma sodium starch glycolate, Gormaso dry flowing starch, L-HPC 21 and pregelatinized starch (SEPISTAB®) of ISISA, BASF crospovidone (KOLLIDON CL®), FMC Foret microcrystalline cellulose (AVICEL PH 101 and AVICEL PH 102®) and a Rohm Pharma high-viscosity acrylic derivative consisting of a copolymer of methacrylic acid and methyl methacrylate in a ratio of approximately 7:3.

EXAMPLE 1

Dispersible tablets were prepared from the following pharmaceutical formula:

| COMPONENTS | WEIGHT (mg) | % BY WEIGHT |
| --- | --- | --- |
| FLUOXETINE HYDROCHLORIDE | 20 | 6.7 |
| SODIUM STARCH GLYCOLATE | 50 | 16.66 |
| LACTOSE | 123 | 40.97 |
| L-HPC 21 | 75 | 25.00 |
| SODIUM SACCHARIN | 2 | 0.67 |
| MINT AROMA | 30 | 10.00 |

The process begins with the weighing of all the raw materials separately then screening them through a screen of 1.19 mm mesh, as a security measure. After screening, the excipients are placed in a suitable mixer, the active ingredient is then added and mixing takes place again until homogenous.

The mixed powders is passed several times through a 0.5 mm mesh screen. Compression follows, with periodic controls during the process and noting the results obtained on the associated control cards. The powder flows satisfactorily and compresses without difficulties. At the end of the process, representative samples are taken for analysis (from the beginning, middle and end of the batch) according to a statistical sampling procedure.

Dispersible tablets were obtained with the following characteristics:
Individual tablet weight: 300 mg±5%
Weight of 10 tablets: 3 g±3%
Hardness: 3–6 Kgf
Height: approximately 2.4 mm
Diameter: 12.25 mm
Disintegration in water at 19° C.–21° C.: <3 min

EXAMPLE 2

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20 | 4.02 |
| SODIUM STARCH GLYCOLATE | 50 | 10.00 |
| PREGELATINIZED STARCH | 337 | 67.38 |
| L-HPC 21 | 25 | 5.00 |
| SODIUM SACCHARIN | 3 | 0.60 |
| MINT AROMA | 50 | 10.00 |
| TITANIUM DIOXIDE | 15 | 3.00 |

The procedure of Example 1 was used, except that the mixed powder was screened in a screen of 0.8 mm mesh (as opposed to 0.5 mm). The powder flows satisfactorily and compresses without difficulties. Dispersible tablets were obtained with the following characteristics:

Individual tablet weight: 500 mg±5%
Weight of 10 tablets: 5 g±3%
Hardness: 5.5 Kgf
Height: approximately 3.6 mm
Diameter: 12.25 mm
Disintegration in water at 19° C.–21° C.: <3 min

EXAMPLE 3

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20.1 | 4.47 |
| SODIUM STARCH GLYCOLATE | 45.0 | 10.00 |
| CMC*, AVICEL PH101 | 162.7 | 36.155 |
| DRY FLOWING STARCH | 162.7 | 36.155 |
| L-HPC 21 | 22.5 | 5.00 |
| SODIUM SACCHARIN | 3.0 | 0.67 |
| PEPPERMINT AROMA | 10.0 | 2.22 |
| TITANIUM DIOXIDE | 15.0 | 3.33 |
| STEARYL SODIUM FUMARATE | 4.5 | 1.00 |
| COLLOIDAL SILICONE DIOXIDE | 4.5 | 1.00 |

*CMC Microcrystalline cellulose

The procedure of Example 2 was used. The powder flows satisfactorily and compresses without difficulties. Dispersible tablets were obtained with the following characteristics:

Individual tablet weight: 450 mg±5%
Weight of 10 tablets: 4.5 g±3%
Hardness: 7 Kgf
Height: approximately 3.3 mm
Diameter: 12.25 mm
Disintegration in water at 19° C.–21° C.: <3 min

EXAMPLE 4

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20 | 4.46 |
| SODIUM STARCH GLYCOLATE | 45 | 10.00 |
| DRY FLOWING STARCH | 121 | 26.89 |
| CMC*, AVICEL PH101 | 242 | 53.76 |
| SODIUM SACCHARIN | 3 | 0.67 |
| PEPPERMINT AROMA | 10 | 2.22 |
| STEARYL SODIUM FUMARATE | 4.5 | 1.00 |
| COLLOIDAL SILICONE DIOXIDE | 4.5 | 1.00 |

*CMC Microcrystalline cellulose

The procedure of Example 2 was used. The powder flows satisfactorily and compresses without difficulties. Dispersible tablets were obtained with the following characteristics:

Individual tablet weight: 450 mg±5%
Weight of 10 tablets: 4.5 g±3%
Hardness: 5.2 Kgf
Height: approximately 3.7 mm
Diameter: 12.25 mm
Disintegration in water at 19° C.–21° C.: <2 min

EXAMPLE 5

Dispersible tablets were prepared from the following pharmaceutical formula:

| COMPONENT | WEIGHT (mg) | % BY WEIGHT |
| --- | --- | --- |
| FLUOXETINE HYDROCHLORIDE | 20.1 | 5.74 |
| SODIUM STARCH GLYCOLATE | 35 | 10.00 |
| DRY FLOWING STARCH | 93.63 | 26.75 |
| CMC*, AVICEL PH102 | 187.27 | 53.51 |
| SODIUM SACCHARIN | 2 | 0.57 |
| PEPPERMINT AROMA | 5 | 1.43 |
| STEARYL SODIUM FUMARATE | 3.5 | 1.00 |
| COLLOIDAL SILICONE DIOXIDE | 3.5 | 1.00 |

*CMC Microcrystalline cellulose

The procedure of Example 2 was used. The powder flows satisfactorily and compresses without difficulties. Dispersible tablets were obtained with the following characteristics:
Individual tablet weight: 350 mg±5%
Weight of 10 tablets: 3.5 g±3%
Hardness: 5.0 Kgf
Height: approximately 2.3 mm
Diameter: 12.25 mm
Disintegration in water at 19° C.–21° C.: <2 min

EXAMPLE 6

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20.1 | 5.60 |
| SODIUM STARCH GLYCOLATE | 35 | 9.75 |
| DRY FLOWING STARCH | 79.4 | 22.12 |
| CMC*, AVICEL PH102 | 200 | 55.71 |
| SODIUM SACCHARIN | 4 | 1.11 |
| PEPPERMINT AROMA | 10 | 2.79 |
| STEARYL SODIUM FUMARATE | 5.25 | 1.46 |
| COLLOIDAL SILICONE DIOXIDE | 5.25 | 1.46 |

*CMC Microcrystalline cellulose

The procedure of Example 2 was used. The powder flows satisfactorily and compresses without difficulties. Dispersible tablets were obtained with the following characteristics:
Individual tablet weight: 359 mg±5%
Weight of 10 tablets: 3.59 g±3%
Hardness: 5.5 Kgf
Height: approximately 2.8 mm
Diameter: 12.25 mm
Disintegration in water at 19° C.–21° C.: <2 min
Friability: 0.5%

EXAMPLE 7

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20.1 | 5.74 |
| ACRYLIC DERIVATE (high viscosity) | 35 | 10.00 |
| CMC*, AVICEL PH102 | 265.5 | 75.86 |
| TITANIUM DIOXIDE | 5.25 | 1.50 |
| SODIUM SACCHARIN | 1.4 | 0.40 |
| PEPPERMINT AROMA | 10.5 | 3.00 |
| STEARYL SODIUM FUMARATE | 7 | 2.00 |
| COLLOIDAL SILICONE DIOXIDE | 5.25 | 1.50 |

*CMC Microcrystalline cellulose

The procedure of Example 2 was used. The powder flows satisfactorily and compresses without difficulties. Dispersible tablets were obtained with the following characteristics:
Individual tablet weight: 359 mg±5%
Weight of 10 tablets: 3.5 g±3%
Hardness: 9.0 Kp
Disintegration in water at 19° C.–21° C.: <3 min
Friability: <0.5%

EXAMPLE 8

Dispersible tablets were prepared from the following pharmaceutical formula:

| COMPONENT | WEIGHT (mg) | % BY WEIGHT |
| --- | --- | --- |
| FLUOXETINE HYDROCHLORIDE | 20.1 | 6.18 |
| ACRYLIC DERIVATE (high viscosity) | 67 | 20.60 |
| CMC*, AVICEL PH102 | 201 | 61.79 |
| TITANIUM DIOXIDE | 10.72 | 3.30 |
| SODIUM SACCHARIN | 1.34 | 0.41 |
| PEPPERMINT AROMA | 10.05 | 3.08 |
| STEARYL SODIUM FUMARATE | 8.38 | 2.58 |
| COLLOIDAL SILICONE DIOXIDE | 6.7 | 2.06 |

*CMC Microcrystalline cellulose

The procedure of Example 2 was used. The powder flows satisfactorily and compresses without difficulties. Dispersible tablets were obtained with the following characteristics:
Individual tablet weight: 325.29 mg±5%
Weight of 10 tablets: 3.25 g±3%
Hardness: 9.0–11.0 Kp
Disintegration in water at 19° C.–21° C.: <3 min
Friability: <0.5%

EXAMPLE 9

Dispersible tablets were prepared from the following pharmaceutical formulation:

| COMPONENT | WEIGHT (mg) | % BY WEIGHT |
| --- | --- | --- |
| FLUOXETINE HYDROCHLORIDE | 20.1 | 6.22 |
| DRY FLOWING STARCH | 69.63 | 21.56 |
| CROSPOVIDONE | 31.5 | 9.75 |
| CMC*, AVICEL PH102 | 175.49 | 54.29 |
| SODIUM SACCHARIN | 3.15 | 0.97 |
| ORANGE AROMA | 13.86 | 4.29 |
| STEARYL SODIUM FUMARATE | 4.73 | 1.46 |
| COLLOIDAL SILICONE DIOXIDE | 4.73 | 1.46 |

*CMC Microcrystalline cellulose

The procedure of Example 2 was used. The powder flows satisfactorily and compresses without difficulties. Dispersible tablets were obtained with the following characteristics:
Individual tablet weight: 323.24 mg±5%
Weight of 10 tablets: 3.23 g±3%
Hardness: 9.0–11.0 Kp
Disintegration in water at 19° C.–21° C.: <3 min
Friability: <0.5%

EXAMPLE 10

Dispersible tablets were prepared from the following pharmaceutical formulation:

| COMPONENT | WEIGHT (mg) | % BY WEIGHT |
|---|---|---|
| FLUOXETINE HYDROCHLORIDE | 20.1 | 6.23 |
| DRY FLOWING STARCH | 69.63 | 21.60 |
| CROSPOVIDONE | 31.5 | 9.76 |
| CMC*, AVICEL PH102 | 175.49 | 54.39 |
| ASPARTAME | 5.36 | 1.66 |
| ORANGE AROMA | 11.03 | 3.42 |
| STEARYL SODIUM FUMARATE | 4.73 | 1.47 |
| COLLOIDAL SILICONE DIOXIDE | 4.73 | 1.47 |

*CMC Microcrystalline cellulose

The procedure of Example 2 was used. The powder flows satisfactorily and compresses without difficulties. Dispersible tablets were obtained with the following characteristics:
Individual tablet weight: 322.62 mg±5%
Weight of 10 tablets: 3.22 g±3%
Hardness: 9.0–11.0 Kp
Disintegration in water at 19° C.–21° C.: <3 min
Friability: <0.5%

EXAMPLE 11

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.93 |
| DRY FLOWING STARCH | 67 | 19.90 |
| CROSPOVIDONE | 33.5 | 9.95 |
| CMC*, AVICEL PH102 | 174.2 | 51.73 |
| SACCHARIN | 15 | 4.45 |
| STEARYL SODIUM FUMARATE | 5.03 | 1.50 |
| COLLOIDAL SILICONE DIOXIDE | 5.03 | 1.50 |
| MANNITOL | 9 | 2.67 |
| LEMON AROMA | 8 | 2.37 |

*CMC Microcrystalline cellulose

The procedure of Example 2 was used. The powder flows satisfactorily and compresses without difficulties. Dispersible tablets were obtained with the following characteristics:
Individual tablet weight: 336.76 mg±5%
Weight of 10 tablets: 3.36 g±3%
Hardness: 9.0–11.0 Kp
Disintegration in water at 19° C.–21° C.: <3 min
Friability: <0.5%

EXAMPLE 12

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.65 |
| DRY FLOWING STARCH | 63.54 | 17.95 |
| CROSPOVIDONE | 35.3 | 9.97 |
| CMC*, AVICEL PH102 | 176.5 | 49.87 |
| SACCHARIN | 8 | 2.26 |
| STEARYL SODIUM FUMARATE | 5.3 | 1.50 |
| COLLOIDAL SILICONE DIOXIDE | 5.3 | 1.50 |
| APRICOT AROMA | 40 | 11.30 |

*CMC Microcrystalline cellulose

The procedure of Example 2 was used. The powder flows satisfactorily and compresses without difficulties. Dispersible tablets were obtained with the following characteristics:
Individual tablet weight: 353.94 mg±5%
Weight of 10 tablets: 3.53 g±3%
Hardness: 9.0–11.0 Kp
Disintegration in water at 19° C.–21° C.: <3 min
Friability: <0.5%

EXAMPLE 13

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.65 |
| DRY FLOWING STARCH | 63.54 | 17.95 |
| CROSPOVIDONE | 35.3 | 9.97 |
| CMC*, AVICEL PH102 | 176.5 | 49.87 |
| SACCHARIN | 3 | 2.26 |
| STEARYL SODIUM FUMARATE | 5.3 | 1.50 |
| COLLOIDAL SILICONE DIOXIDE | 5.3 | 1.50 |
| STRAWBERRY AROMA | 40 | 11.30 |

*CMC Microcrystalline cellulose

The procedure of Example 2 was used. The powder flows satisfactorily and compresses without difficulties. Dispersible tablets were obtained with the following characteristics:
Individual tablet weight: 353.94 mg±5%
Weight of 10 tablets: 3.53 g±3%
Hardness: 9.0–11.0 Kp
Disintegration in water at 19° C.–21° C.: <3 min
Friability: <0.5%

EXAMPLE 14

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.65 |
| DRY FLOWING STARCH | 63.54 | 17.95 |
| CROSPOVIDONE | 35.3 | 9.97 |
| CMC*, AVICEL PH102 | 176.5 | 49.87 |
| SACCHARIN | 8 | 2.26 |
| STEARYL SODIUM FUMARATE | 5.3 | 1.50 |
| COLLOIDAL SILICONE DIOXIDE | 5.3 | 1.50 |
| PEACH AROMA | 40 | 11.30 |

*CMC Microcrystalline cellulose

The procedure of Example 2 was used. The powder flows satisfactorily and compresses without difficulties. Dispersible tablets were obtained with the following characteristics:
Individual tablet weight: 353.94 mg±5%
Weight of 10 tablets: 3.53 g±3%
Hardness: 9.0–11.0 Kp
Disintegration in water at 19° C.–21° C.: <3 min
Friability: <0.5%

EXAMPLE 15

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.65 |
| DRY FLOWING STARCH | 63.54 | 17.95 |
| CROSPOVIDONE | 35.3 | 9.97 |
| CMC*, AVICEL PH102 | 176.5 | 49.87 |

| COMPONENT | WEIGHT (mg) | % BY WEIGHT |
|---|---|---|
| SACCHARIN | 8 | 2.26 |
| STEARYL SODIUM FUMARATE | 5.3 | 1.50 |
| COLLOIDAL SILICONE DIOXIDE | 5.3 | 1.50 |
| PINEAPPLE AROMA | 20 | 5.65 |
| COCONUT AROMA | 20 | 5.65 |

*CMC Microcrystalline cellulose

The procedure of Example 2 was used. The powder flows satisfactorily and compresses without difficulties. Dispersible tablets were obtained with the following characteristics:
Individual tablet weight: 353.94 mg±5%
Weight of 10 tablets: 3.53 g±3%
Hardness: 9.0–11.0 Kp
Disintegration in water at 19° C.–21° C.: <3 min
Friability: <0.5%

EXAMPLE 16

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.65 |
| DRY FLOWING STARCH | 63.54 | 17.95 |
| CROSPOVIDONE | 35.3 | 9.97 |
| CMC*, AVICEL PH102 | 176.5 | 49.87 |
| SACCHARIN | 8 | 2.26 |
| STEARYL SODIUM FUMARATE | 5.3 | 1.50 |
| COLLOIDAL SILICONE DIOXIDE | 5.3 | 1.50 |
| LEMON AROMA | 40 | 11.30 |

*CMC Microcrystalline cellulose

The procedure of Example 2 was used. The powder flows satisfactorily and compresses without difficulties. Dispersible tablets were obtained with the following characteristics:
Individual tablet weight: 353.94 mg±5%
Weight of 10 tablets: 3.53 g±3%
Hardness: 9.0–11.0 Kp
Disintegration in water at 19° C.–21° C.: <3 min
Friability: <0.5%

EXAMPLE 17

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.48 |
| DRY FLOWING STARCH | 58 | 15.9 |
| CROSPOVIDONE | 35.3 | 9.7 |
| CMC*, AVICEL PH102 | 175 | 47.9 |
| SACCHARIN | 5 | 1.4 |
| MANNITOL | 13 | 3.6 |
| SORBITOL | 8 | 2.2 |
| STEARYL SODIUM FUMARATE | 5.3 | 1.4 |
| COLLOIDAL SILICONE DIOXIDE | 5.3 | 1.4 |
| STRAWBERRY AROMA | 40 | 10.96 |

*CMC Microcrystalline cellulose

The procedure of Example 2 was used. The powder flows satisfactorily and compresses without difficulties. Dispersible tablets were obtained with the following characteristics:
Individual tablet weight: 364.9 mg±5%
Weight of 10 tablets: 3.64 g±3%
Hardness: 9.0–11.0 Kp
Disintegration in water at 19° C.–21° C.: <3 min
Friability: <0.5%

EXAMPLE 18

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.9 |
| DRY FLOWING STARCH | 50 | 14.8 |
| CROSPOVIDONE | 37 | 11 |
| CMC*, AVICEL PH102 | 155 | 46 |
| SACCHARIN | 5 | 1.5 |
| MANNITOL | 13 | 3.9 |
| SORBITOL | 6 | 1.8 |
| STEARYL SODIUM FUMARATE | 5.3 | 1.6 |
| COLLOIDAL SILICONE DIOXIDE | 5.3 | 1.6 |
| STRAWBERRY AROMA | 40 | 11.9 |

*CMC Microcrystalline cellulose

The procedure of Example 2 was used. The powder flows satisfactorily and compresses without difficulties. Dispersible tablets were obtained with the following characteristics:
Individual tablet weight: 336.6 mg±5%
Weight of 10 tablets: 3.36 g±3%
Hardness: 9.0–11.0 Kp
Disintegration in water at 19° C.–21° C.: <3 min
Friability: <0.5%

EXAMPLE 19

Dispersible tablets were prepared from the following pharmaceutical formulation:

| COMPONENT | WEIGHT (mg) | % BY WEIGHT |
|---|---|---|
| FLUOXETINE HYDROCHLORIDE | 20 | 5.92 |
| DRY FLOWING STARCH | 50 | 14.80 |
| CROSPOVIDONE | 37 | 10.95 |
| CMC*, AVICEL PH102 | 155 | 45.91 |
| SACCHARIN | 3 | 0.88 |
| MANNITOL | 13 | 3.84 |
| SORBITOL | 6 | 1.76 |
| AMMONIUM GLYCIRICINATE | 3 | 0.88 |
| STEARYL SODIUM FUMARATE | 5.3 | 1.56 |
| COLLOIDAL SILICONE DIOXIDE | 5.3 | 1.56 |
| STRAWBERRY AROMA | 40 | 11.84 |

*CMC Microcrystalline cellulose

The procedure of Example 2 was used. The powder flows satisfactorily and compresses without difficulties. Dispersible tablets were obtained with the following characteristics:
Individual tablet weight: 337.6 mg±5%
Weight of 10 tablets: 3.37 g±3%
Hardness: 9.0–11.0 Kp
Disintegration in water at 19° C.–21° C.: <3 min
Friability: <0.5%

EXAMPLE 20

Dispersible tablets were prepared from the following pharmaceutical formulation:

| COMPONENT | WEIGHT (mg) | % BY WEIGHT |
|---|---|---|
| FLUOXETINE HYDROCHLORIDE | 22.37 | 7.22 |
| DRY FLOWING STARCH | 55.93 | 18.05 |
| CROSPOVIDONE | 41.38 | 13.35 |

| COMPONENT | WEIGHT (mg) | % BY WEIGHT |
|---|---|---|
| CMC*, AVICEL PH102 | 142.66 | 46.02 |
| SACCHARIN | 11.19 | 3.61 |
| MANNITOL | 14.54 | 4.69 |
| SORBITOL | 6.71 | 2.16 |
| STEARYL SODIUM FUMARATE | 5.93 | 1.91 |
| COLLOIDAL SILICONE DIOXIDE | 5.93 | 1.91 |
| ANISEED AROMA | 2.24 | 0.72 |
| PEPPERMINT AROMA | 1.12 | 0.36 |

*CMC Microcrystalline cellulose

The procedure of Example 2 was used. The powder flows satisfactorily and compresses without difficulties. Dispersible tablets were obtained with the following characteristics:

Individual tablet weight: 310 mg±5%
Weight of 10 tablets: 3.10 g±3%
Hardness: 12.0–15.0 kp
Thickness: 42.7–47.2 mm
Disintegration in water at 19° C.–21° C.: <3 min
Friability: <0.5%

I claim:

1. A pharmaceutical formulation suitable for the manufacture of dispersible tablets by direct compression, said tablets dispersible in water at 19°–21° C. in less than three minutes, consisting of fluoxetine or an addition salt thereof, as active ingredient, in a quantity between 4% and 7.5% by weight in relation to the total formulation weight, along with:
   a) a disintegrant selected from the group consisting of sodium starch glycollate, polymeric derivatives of acrylic acid, and crospovidone;
   b) a diluent selected from the group consisting of microcrystalline cellulose, lactose, hydroxypropyl cellulose (HPC), pregelatinized starch, dry flowing starch, and combinations and mixtures thereof;
   c) a lubricant selected from the group consisting of talcum and stearyl sodium fumarate unless the diluent is pregelatinized starch, where the formulation is lubricant free;
   d) colloidal silicon dioxide as an anti-adherent;
   e) artificial or natural sweeteners selected from the group consisting of sodium saccharin, aspartame, mannitol, sorbitol, and ammonium glyciricinate, or mixtures thereof;
   f) a flavoring selected from the group consisting of mint aroma, peppermint aromas, orange flavoring, peach aroma, apricot aroma, raspberry aroma, lemon aroma, coconut aroma, pineapple aroma, strawberry aroma, aniseed, and mixtures thereof; and optionally
   g) titanium dioxide as a colorant.

2. A formulation as set forth in claim 1, containing a quantity of sodium starch glycolate between 9.5% and 17% by weight in relation to the total weight of the formulation.

3. A formulation as set forth in claim 1, containing a quantity of acrylic acid derivatives of between 10% and 21% by weight in relation to the total weight of the formulation.

4. A formulation as set forth in claim 1, containing a quantity of crospovidone of between 9% and 13% by weight in relation to the total weight of the formulation.

5. A formulation as set forth in claim 1, containing a quantity of hydroxypropyl cellulose, preferably L-HPC, of between 5% and 25% by weight in relation to the total weight of the formulation.

6. A formulation as set forth in claim 1, comprising a combination of pregelatinized starch, and hydroxypropyl cellulose, preferably L-HPC, containing a quantity of pregelatinized starch of between 60% and 70% by weight in relation to the total weight of the formulation, and a quantity of HPC of approximately 5% by weight in relation to the total weight of the formulation.

7. A formulation as set forth in claim 1, containing a quantity of microcrystalline cellulose of between 62% and 76% by weight in relation to the total weight of the formulation.

8. A formulation as set forth in claim 7, wherein said microcrystalline cellulose has a mean particle size of between 50 and 90 microns.

9. A formulation as set forth in claim 1, comprising a combination of microcrystalline cellulose and dry flowing starch, with a quantity of dry flowing starch of between 15% and 27% by weight in relation to the total weight of the formulation, and a quantity of microcrystalline cellulose of between 46% and 58% by weight in relation to the total weight of the formulation.

10. A formulation as set forth in claim 1, containing a quantity of stearyl sodium fumarate as lubricant of between 1% and 2.5% by weight in relation to the total weight of the formulation.

11. A formulation as set forth in claim 1, containing as anti-adherent a quantity of colloidal silicone dioxide of between 1% and 2% by weight in relation to the total weight of the formulation.

12. A formulation as set forth in claim 1, containing a quantity of sodium saccharin as artificial sweetener of between 0.4% and 5% by weight in relation to the total weight of the formulation, or a quantity of aspartame of approximately 1.6% by weight in relation to the total weight of the formulation.

13. A formulation as set forth in claim 1, containing a quantity of mannitol of between 2.5% and 5% by weight in relation to the total weight of the formulation.

14. A formulation as set forth in claim 1, containing a quantity of sorbitol of between 1.5% and 4% by weight in relation to the total weight of the formulation.

15. A formulation as set forth in claim 1, containing a quantity of ammonium glyiricinate of between 0.5% and 1% by weight in relation to the total weight of the formulation.

16. A formulation as set forth in claim 1, comprising a mixture of sodium saccharin and mannitol containing a quantity of sodium saccharin of between 0.5% and 4.5% by weight in relation to the total weight of the formulation, and a quantity of mannitol of between 2.5% and 5% by weight in relation to the total weight of the formulation.

17. A formulation as set forth in claim 1 comprising, as flavorings, mint aroma, peppermint aromas, orange flavoring, peach aroma, apricot aroma, raspberry aroma, lemon aroma, coconut aroma and pineapple aroma, or their mixtures, in quantities of between 1.4% and 12.5% by weight in relation to the total weight of the formulation.

18. A formulation as set forth in claim 1, containing a quantity of mannitol and sorbitol as sweetener, and a flavoring comprising strawberry aroma, of between 10% and 12% by weight in relation to the weight of the formulation; or a quantity of aniseed of between 0.6% and 0.7% by weight in relation to the weight of the formulation; or a quantity of peppermint of approximately 0.3% by weight of the formulation; or combinations of the last two.

19. A formulation as set forth in claim 1, wherein the acid addition salt of fluoxetine is the hydrochloride.

20. A dispersible tablet containing fluoxetine or an acid addition salt thereof, obtainable by direct compression of a pharmaceutical formulation of claim 1.

* * * * *